(12) United States Patent
Kumar et al.

(10) Patent No.: US 7,052,886 B2
(45) Date of Patent: May 30, 2006

(54) PROCESS FOR THE ISOLATION OF LOVASTATIN

(75) Inventors: Parveen Kumar, Haryana (IN); Srinivasan Raman, Haryana (IN); Pardeep Narula, Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 92 days.

(21) Appl. No.: 10/311,944

(22) PCT Filed: Jun. 20, 2001

(86) PCT No.: PCT/IB01/01087

§ 371 (c)(1), (2), (4) Date: Apr. 24, 2003

(87) PCT Pub. No.: WO02/00615

PCT Pub. Date: Jan. 3, 2002

(65) Prior Publication Data

US 2003/0215932 A1    Nov. 20, 2003

(30) Foreign Application Priority Data

Jun. 30, 2000   (IN)   ............... 630/DEL/2000

(51) Int. Cl.
*C12P 17/06* (2006.01)
*C12P 17/02* (2006.01)

(52) U.S. Cl. .................... 435/125; 435/123

(58) Field of Classification Search ........... 435/125, 435/123
See application file for complete search history.

(56) References Cited

U.S. PATENT DOCUMENTS

| 4,231,938 A | 11/1980 | Monaghan et al. ...... 260/343.5 |
| 4,319,039 A | 3/1982 | Albers-Schonberg ....... 560/256 |
| 4,432,996 A | 2/1984 | Gullo et al. ................ 424/311 |
| 5,403,728 A | 4/1995 | Jekkel et al. ............... 435/125 |
| 5,712,130 A * | 1/1998 | Hajko et al. ................ 435/123 |
| 5,763,646 A | 6/1998 | Kumar et al. ............... 560/252 |
| 6,825,015 B1 * | 11/2004 | Pfaum et al. ............... 435/125 |

FOREIGN PATENT DOCUMENTS

| DE | 30 06 216 | 11/1980 |
| EP | 0 033 536 | 9/1984 |
| JP | WO 01/00606 | 1/2001 |
| WO | WO 97/20834 | 6/1997 |
| WO | 035515 A1 * | 4/2005 |

OTHER PUBLICATIONS

Blackwell C M et al, "Total Synthesis of Dihydromevinolin and a Series Related 3-Hydroxy-3-Methylglutaryl Coenzyme A Reductase Inhibitors", Journal of Organic Chemistry, American Chemical Society, Washington, DC, US, vol. 57, No. 21, 1992, pp. 5596-5606.

* cited by examiner

*Primary Examiner*—Herbert J. Lilling
(74) *Attorney, Agent, or Firm*—Jayadeep R. Deshmukh, Esq.; George E. Heibel, Esq.

(57) ABSTRACT

The process for the preparation and isolation of the hypolipaemic active substance lovastatin in substantially pure form having a purity of at least 95% which comprises lactonizing the mevinolinic acid to lovastatin in a totally aqueous medium.

11 Claims, No Drawings

PROCESS FOR THE ISOLATION OF LOVASTATIN

FIELD OF THE INVENTION

The present invention relates to a process for the preparation and isolation of the hypolipaemic active substance lovastatin in substantially pure form having a purity of at least 95% which comprises lactonizing the mevinolinic acid of Formula II

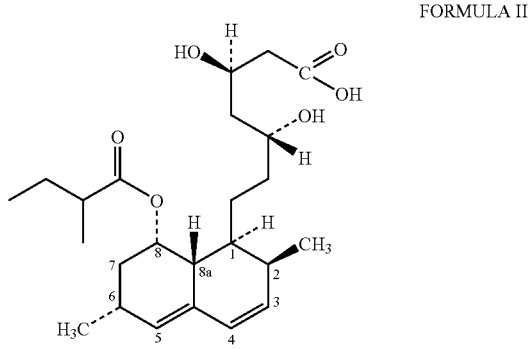

FORMULA II to lovastatin of Formula I

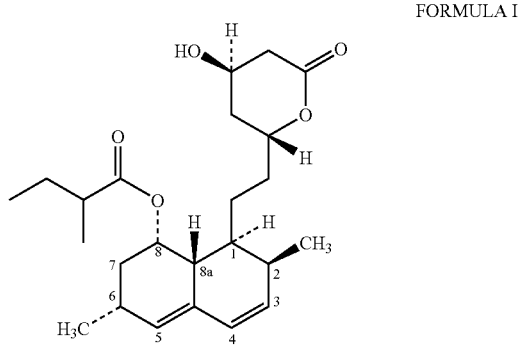

FORMULA I in a totally aqueous medium.

BACKGROUND OF THE INVENTION

It is known that certain mevalonate derivatives are active as anti-hyper-cholesterolemic agents, and these function by limiting cholesterol biosynthesis by inhibiting the enzyme HMG-CoA reductase. Lovastatin, Pravastatin, Simvastatin, Mevastatin, Atorvastatin and derivatives and analogs thereof are known as HMG-COA reductase inhibitors and are used as anti-hypercholesterolemic agents. The majority of them are produced by fermentation using microorganisms of different species belonging to *Aspergillus, Monascus, Nocardia, Amycolatopsis, Mucor* or *Penicillium* genus; others are obtained by treating the fermentation products using the method of chemical synthesis or they are the product of total chemical synthesis.

Lovastatin is the first of the statins to be used widely and is manufactured by a fermentation-based process. It is produced as a secondary metabolite of the fungus *Aspergillus terreus* (U.S. Pat. No. 4,231,938) deposited in American Type Culture Collection under Nos. ATCC 20541 and ATCC 20542, and *Monascus ruber* deposited in Fermentation Research Institute Agency of Industrial Science and Technology, Ministry of International Trade and Industry, Japan (DE 3006216 Al) under No. Ferm. 4822.

Chemically lovastatin is 1,2,6,7,8,8a-hexahydro-β,δ-dihydroxy-2,6-dimethyl-8-(2-methyl-1-oxobutoxy)-1-naphthalene heptanoic acid δ-lactone of Formula I:

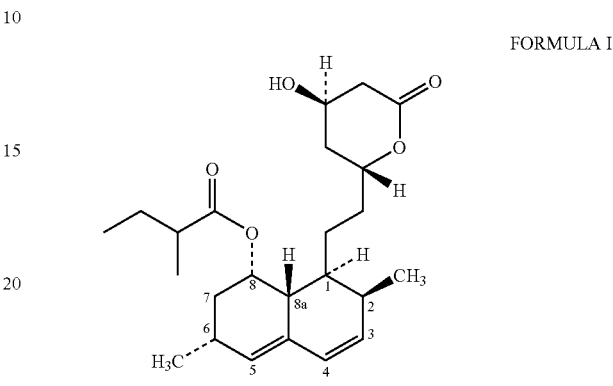

FORMULA I

An active form of lovastatin is an acid, which is chemically 1,2,6,7,8,8a-hexahydro-β,δ-dihydroxy-2,6-dimethyl-8-(2-methyl-1-oxobutoxy)-1-naphthalene heptanoic acid of Formula II:

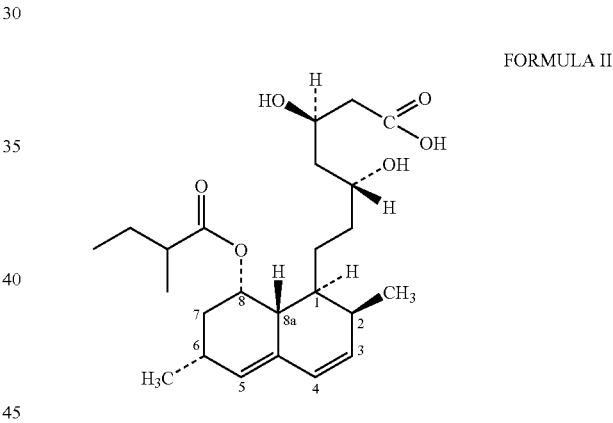

FORMULA II

The recent commercial introduction of chemically synthesised HMG-CoA reductase inhibitors has provided a need for the development of high yielding processes for production of fermentation-based statins. The techniques to improve the processes include, but are not limited to, improving the producer microorganism, scale-up of the process, improving the culture medium or simplifying the downstream recovery process.

In the fermentation broth, lovastatin is present mostly in its hydroxy acid form, mevinolinic acid. The isolation of lovastatin from the fermentation broth, can be categorised into two routes in the prior art processes. The first route comprises of solvent extraction of mevinolinic acid and isolation of ammonium salt of mevinolinic acid as an intermediate and its further lactonization to lovastatin (U.S. Pat. No. 4,319,039).

The second route comprises of solvent extraction of mevinolinic acid, lactonization in the solvent phase and isolation as lovastatin (PCT publication WO 97/20834). The isolation of lovastatin as disclosed in EP 033536 comprises of extraction of the broth with ethyl acetate. The extract is concentrated by vacuum distillation followed by lactonization in toluene at 106° C. for 2 hours. After the lactonization is complete, the solution is concentrated to a small volume and then subjected to column chromatography using solvents like ethyl acetate or n-hexane and the collected fractions are again concentrated in vacuum and then pure lovastatin crystallizes in the lactone form.

Both the routes may employ a final purification step to obtain lovastatin of pharmacopoeial grade.

The process for the isolation and purification of anti-hypercholesterolemic agents disclosed in the earlier patents have certain inherent disadvantages and involves a number of steps which include multiple solvent extractions, chromatography, lactonization and crystallization methods. Although, the purity of the final product obtained by these procedures is of pharmacopoeial standards yet, the yields of the desired product are relatively low. In addition, they require both large amounts of organic solvents and correspondingly large equipment suited for these quantities. The second route involves lactonization at higher temperature in the solvent phase necessitating elaborate purification step(s) for removal of undesirable impurities generated during the lactonization step.

Neither of the methods heretofore described is completely satisfactory for the above-stated reasons.

SUMMARY OF THE INVENTION

It is an object of the present invention to solve the problems associated with the prior art and to provide a simplified and efficient method for the preparation of lovastatin, leading to an economically-more attractive method of manufacturing. The process, in addition, also yields higher quality product.

The present invention solves the drawbacks of the processes known in the prior art as it enables to obtain the pure lovastatin by a process, which process is less time consuming and provides higher yields using fewer number of solvents. The process is more nature friendly, is not demanding in terms of space and energy and thus, enables an economical large scale production.

The present invention specifically describes a process for effecting the lactonization of mevinolinic acid of Formula II

FORMULA II in the aqueous medium and isolating the corresponding lovastatin of Formula I:

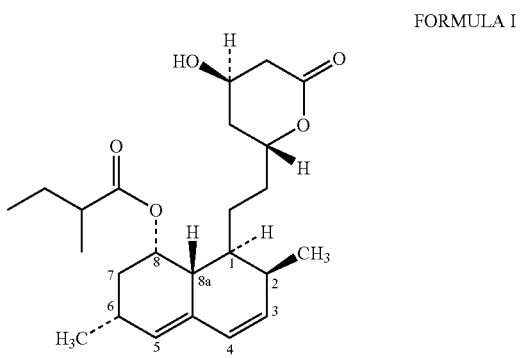

FORMULA I in substantially pure form from the solution thereof. The lactonization is effected in a totally aqueous medium, the fermentation broth itself. Lovastatin, so obtained is in substantially pure form and has a chromatographic purity of at least 95%.

According to the present invention, lovastatin is derived from the fermentation broth which comprises of the microorganism preferably a fungus belonging to the genus *Aspergillus,* preferably *Aspergillus terreus* (ATCC 20542) or its hyperproducer thereof.

The process comprises lowering the pH of the fermented broth containing lovastatin, present mostly in the form of mevinolinic acid to 2.0 to 3.0, and incubating the broth for about 20–60 hours at a temperature from about 40–60° C. affecting the lactonization of mevinolinic acid and recovering the corresponding lovastatin from the solution thereof. The acid for lowering the pH may be selected from the commonly used acids, preferably the mineral acids like hydrochloric acid, sulfuric acid, nitric acid, phosphoric acid, etc.

In a preferred embodiment, the broth is incubated for 24 hours. In a further preferred embodiment, the broth is incubated at a temperature in the range of 40–60° C., most preferable being 50–60° C.

The subsequent isolation of lovastatin is carried out by conventional methods known in the art to a person of ordinary skill. Lovastatin is isolated from the solution by extracting it with a solvent followed by concentration of solvent, crystallization and drying the product. Solvent which may be used is generally selected from esters such as ethyl acetate, butyl acetate or aromatic hydrocarbons such as toluene. Methods known in the art may be used with the process of this invention to enhance any aspect of this process. For example, lovastatin obtained may further be purified. The purification can be such as recrystallization from solvents.

DETAILED DESCRIPTION OF THE INVENTION

The following specific examples illustrate the process of present invention, but they are not intended to limit the scope of the invention.

EXAMPLE 1

To 6.2 L of fermentation broth, 0.80 L of dilute sulfuric acid (2N) was added to bring the pH to 2.1. The acidified broth was heated to about 50° C. and was stirred at 50–60° C. for about 24 hours. 90% of the acid form was converted to lactone form as monitored by High Pressure Liquid Chromatography.

The broth was filtered and the mycelial cake was extracted with 7.5 L of toluene. The toluene extract was washed with 1.3 L of 5% w/v sodium bicarbonate solution and 0.65 L of demineralised water. The washed toluene extract was concentrated under vacuum at about 60° C., to a volume of about 160–200 mL. The concentrate was cooled to 5–7° C. and stirred further for 1 hour. The slurry was then filtered and the cake was washed with 50 mL of pre-cooled (5–10° C.) toluene. The wet cake was dried at 40° C. under vacuum for 16 hours. 25.6 g of Lovastatin with a chromatographic purity of more than 95% was obtained.

EXAMPLE 2

To 12 L of fermentation broth, 1.40 L of dilute nitric acid (10%) was added to bring the pH to 2.2. The acidified broth was heated to about 50° C. and was stirred at this temperature for about 48 hours. 90% of the acid form was converted to lactone form as monitored by High Pressure Liquid Chromatography.

The broth was filtered and the mycelial cake was extracted with 12 L of toluene. The toluene extract was washed with 1.5 L of 5% w/v sodium bicarbonate solution and 1.5 L of demineralised water. The washed toluene extract was concentrated under vacuum at about 50° C., to a volume of about 300–350 mL. The concentrate was cooled to 5–7° C. and stirred at this temperature for 3 hours. The slurry was then filtered and the cake was washed with 100 mL of pre-cooled (5–10° C.) toluene. The wet cake was dried at 40° C. under vacuum. 46.2 g of Lovastatin with a chromatographic purity of more than 95% was obtained.

EXAMPLE 3

To 8500 L of fermentation broth, 540 L of dilute sulfuric acid (2N) was added to bring the pH to 2.0. The acidified broth was heated to 50–55° C. and was stirred further for about 22 hours. More than 90% of the acid form was converted to lactone form, as monitored by High Pressure Liquid Chromatography.

The whole broth was extracted with 7600 L of toluene. The toluene extract was washed with 1340 L of 5% w/v sodium bicarbonate solution and 670 L of demineralised water. The washed toluene extract was concentrated under vacuum at 40–60° C., to a volume of approximately 200 L. The concentrate was cooled to 5–8° C. and stirred further for 2 hours. The slurry was then filtered and the cake was washed with 130 L of pre-cooled (5–10° C.) toluene. The wet cake was dried to yield 45.3 Kg of Lovastatin with a chromatographic purity of more than 95%.

While the present invention has been described in terms of its specific embodiments, certain modifications and equivalents will be apparent to those skilled in the art and are intended to be included within the scope of the present invention.

We claim:

1. A process for effecting the lactonization of mevinolinic acid of Formula II

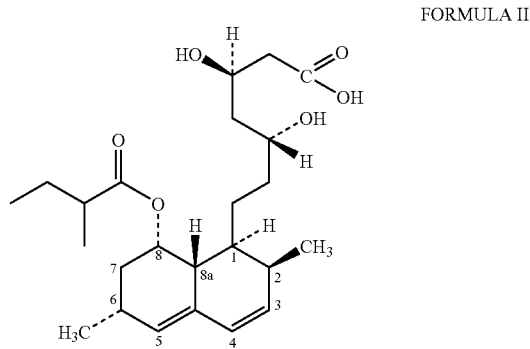

FORMULA II in an aqueous medium, the process lowering the pH of a fermentation broth and isolating the corresponding lovastatin of Formula I so obtained

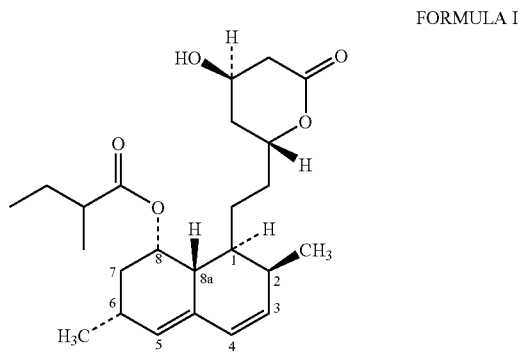

FORMULA I in substantially pure form.

2. The process of claim 1, wherein the fermentation broth is incubated at a temperature of from about 40–60° C.

3. The process of claim 2, wherein the fermentation broth comprises of the microorganism capable of producing lovastatin.

4. The process of claim 3, wherein the microorganism is a fungus.

5. The process of claim 4, wherein the fungus belongs to the genus *Aspergillus*.

6. The process of claim 5, wherein the fungus is *Aspergillus terreus* (ATCC 20542).

7. The process of claim 1, wherein the pH of the fermentation broth is lowered with an acid in the range of 2.0–3.0.

8. The process of claim 7, wherein the acid is a mineral acid.

9. The process of claim 8, wherein the mineral acid is selected from the group consisting of sulfuric acid, nitric acid, hydrochloric acid or phosphoric acid.

10. The process of claim 1, which further comprises isolating the lovastatin from the fermentation broth by extracting with a solvent followed by concentration of solvent extract, crystallization and drying of lovastatin.

11. The process of claim 10, wherein the solvent is selected from esters such as ethyl acetate, butyl acetate or aromatic hydrocarbons such as toluene.

* * * * *